United States Patent [19]

Meyer

[11] Patent Number: 5,750,514
[45] Date of Patent: May 12, 1998

[54] METHOD FOR CONTROLLING ECTOPARASITES

[76] Inventor: Jeffery A. Meyer, 1209 Hampton La., Mundelein, Ill. 60060

[21] Appl. No.: 439,419

[22] Filed: May 11, 1995

[51] Int. Cl.$^6$ ..................................................... A01N 65/00
[52] U.S. Cl. .......................... 514/63; 428/413; 514/67; 514/531; 514/974
[58] Field of Search ................. 514/63, 67, 531, 514/974; 428/413

[56] References Cited

U.S. PATENT DOCUMENTS

| | | | |
|---|---|---|---|
| 2,321,023 | 6/1943 | Goodhue et al. | 514/67 |
| 2,421,570 | 6/1947 | La Forge et al. | 514/67 |
| 2,755,218 | 7/1956 | Beroza | 514/67 |
| 3,055,800 | 9/1962 | Willmore et al. | 514/67 |
| 3,063,893 | 11/1962 | Goldberg | 514/67 |
| 3,264,176 | 8/1966 | Rapport | 514/67 |
| 4,668,666 | 5/1987 | Allan et al. | 514/63 |
| 5,326,560 | 7/1994 | Henderson | 514/67 |

FOREIGN PATENT DOCUMENTS

| | | |
|---|---|---|
| 2132177 | 7/1978 | Australia . |
| 0061208 | 9/1982 | European Pat. Off. . |
| 0273862 | 7/1988 | European Pat. Off. . |
| 9113545 | 9/1991 | WIPO . |

OTHER PUBLICATIONS

Seaman, D., "Trends in the Formulation of Pesticides—An Overview", *Pestic. Sci.*, vol. 29, pp. 437–449 (1990).

*Primary Examiner*—John M. Cooney, Jr.
*Attorney, Agent, or Firm*—Lerner, David, Littenberg, Krumholz & Mentlik

[57] ABSTRACT

An improved method for controlling infestations of flies on an animal wherein a solution of an ectoparasiticide is applied to the skin or coat of the animal comprises increasing the concentration of the ectoparasiticide to about 3% to about 90% of the composition and proportionately reducing the volume of the solution administered to the animal such that the animal receives the same amount of the ectoparasiticide as it would have received prior to the concentration of the solution.

13 Claims, No Drawings

METHOD FOR CONTROLLING ECTOPARASITES

FIELD OF THE INVENTION

This invention relates to an improved method for protecting animals, such as herd animals, from flies. More specifically, the invention relates to an improved method in which a concentration of a composition of an ectoparasiticide is increased to about 3%—about 90% and the volume of the composition applied to the animal is reduced proportionately, such that the animal receives the same amount of the ectoparasiticide active ingredient(s) as it would have received prior to the concentration step.

BACKGROUND OF THE INVENTION

Methods for protecting animals from infestations of ectoparasites, such as horn flies, *Haematobia irritans*, typically involve the application of large volumes of pesticide solutions which contain low concentrations of the insecticide, typically in the range of about 0.5% to about 1.5% of the insecticide. Commonly, the solutions are sprayed or poured onto the coat or fur of the animal and the solutions must contact a large area of the animal in order to be effective for any significant period of time. As an example, a solution often used to combat horn fly infestations of cattle is a pour-on solution of a 1% pyrethroid, such as permethrin, which may be formulated with 1% piperonyl butoxide (synergist).

Each animal can be treated with up to about 150 ml of this solution (depending upon the body weight of the animal) and the solution is effective (greater than 90% reduction) for approximately 21 days.

Although such solutions are beneficial, improvements have been sought. The common practice for increasing the efficacy of an ectoparasiticide applied to animals is to either increase the rate of application of the insecticide or utilize more bioactive materials. Both of these methods have significant disadvantages. Increasing the rate of application exposes the animals and the environment to increased amounts of insecticide, which increases the costs and risks to the environment and to the person applying the insecticide. Finding and developing more bioactive materials has proved to be difficult and also adds to the cost of ectoparasite control.

Accordingly, methods are sought for increasing the efficacy of ectoparasiticides without incurring significant disadvantages and costs.

SUMMARY OF THE INVENTION

The present invention provides an improved method for controlling infestations of flies on an animal wherein a composition comprising an ectoparasiticide in a physiologically acceptable carrier is applied to the skin or coat of the animal. The improvement comprises increasing the concentration of the ectoparasiticide to about 3% to about 90% of the composition and proportionately reducing the volume of the composition administered to the animal such that the animal receives the same amount of the ectoparasiticide as it would have received prior to the concentration and reduction in dose volume.

DETAILED DESCRIPTION OF THE INVENTION

It unexpectedly has been found that the efficacy of ectoparasiticide formulations in combatting infestations of flies can be increased by concentrating the active ingredient in the formulation and then applying a reduced amount of the concentrated formulation to the animal, such that the animal receives the same amount of pesticide as is conventionally applied. In a preferred embodiment, the composition is in the form of a solution, although dry formulations also can be used.

Pesticides which are useful for the formulations of the present invention include compounds of the groups known as organophosphates and pyrethroids. Both groups of compounds are known in the art to possess useful pesticidal properties and have been shown to be effective in combatting infestations of different types of flies, such as horn flies, *Haematobia irritans*, and buffalo flies, *Haematobia exigua*.

Suitable organophosphate pesticides can include phosphate, phosphothioate and phosphothionate compounds. Suitable pyrethroids include either the active insecticidal constituents of pyrethrum flowers or synthetic versions of these compounds. Preferred pesticides suitable for use in the formulations include the organophosphate compound known as pirimiphos-methyl (0-2-diethylamino-6-methylpyrimidin-4-yl dimethyl phosphorothioate) and the synthetic pyrethroid, permethrin (3-(2,2-dichloroethenyl)-2, 2-dimethylcyclopropane-carboxylic acid). Specific examples of organophosphate and pyrethroid compounds that can be used in the formulations are listed in Table A.

TABLE A

| Organophosphate | Pyrethroids |
|---|---|
| Chlorpyriphos | Permethrin |
| Pirimiphos-methyl | Lambdacyhalothrin |
| Diazinon | Natural pyrethrin |
| tetrachlorvinphos | |

In a preferred embodiment, solutions of these ectoparasiticides can be made by mixing the active ingredient in a solvent, such as mineral oil, corn oil, propylene glycol monomethyl ether or dipropylene glycol monomethyl ether, in accordance with conventional procedures, optionally in combination with an insecticide synergist, such as piperonyl butoxide or MGK 264 (n-octyl bicycloheptene dicarboximide, manufactured by McLaughlin Gormley King Company, Minneapolis, Minn.). Generally, solutions that have been used in the art to protect animals from flies have comprised about 0.5% to about 1.5% of ectoparasiticide and, if present, an equal amount of insecticide synergist. The synergists can be combined with either a pyrethroid or organophosphate ectoparasiticide, but most typically are used in combination with the pyrethroids.

The improved solutions of the present invention are prepared by increasing the concentration of pesticide up to about 3% to about 90% weight/weight. Preferably, the concentration is increased to be within the range of about 5% to about 50%, and most preferably to be within the range of about 5% to about 30%. If the solution further comprises a synergist, the concentration of the synergist desirably is increased to at least mirror the increase in concentration of the pesticide. The ratio of synergist to pyrethroids can range from about 5–10:1 to about 1:1.

Following the preparation of the more concentrated solution, the solution is applied to animals in a volume which is reduced proportionately to the increase in concentration. Thus, for example, the art teaches that cattle can be protected from horn flies by applying to each animal 150 ml of a 1% permethrin solution, which further may comprise 1% piperonyl butoxide. In accordance with this invention, the concentration of the ectoparasiticide can be increased from 1% to 5% (a 5X increase) and then only 30 ml (a 5X decrease) need be applied to the cow. Thus, the cow receives the same amount of pesticide as it had before, but receives a lesser amount of solution. Surprisingly, whereas the conventional 1% permethrin solution typically is effective (more than 90% fly reduction) for about 21 days, the smaller application of the more concentrated solution has been found to extend the duration of efficacy to as long as about 42 days.

In an alternative embodiment, the composition can be in dry, rather than liquid, form. Insecticidal powders can be made using, for example, talc or clay as the carrier. As with the solutions described above, the concentration of ectoparasiticide is increased to be within the range of about 3% to about 90%, then the amount of the composition applied to the animal is correspondingly reduced, such that the animal receives the same amount of the ectoparasiticide as conventionally would be applied.

The concentrated compositions of this invention can be applied to animals, such as herd animals, that can be bothered by flies. The compositions can be applied, for example, to cattle, sheep, goats, horses, donkeys, camels, pigs, reindeer, caribou and buffalo.

Surprisingly, the administration of decreased amounts of concentrated ectoparasiticide compositions has not been found to increase the efficacy of the ectoparasiticide in controlling infestations of other ectoparasites, such as lice and ticks. In tests conducted, concentrated compositions of ectoparasiticide were either less effective than, or only as effective as, conventional compositions.

The invention is further described by the following examples, which are not intended to be limiting.

EXAMPLE 1

The efficacy of a pour-on formulation against horn flies was evaluated as follows:

Herds of beef cattle were segregated by pasture and treated with one of the following formulations: (1) control (no insecticide treatment); (2) 5% permethrin+5% piperonyl butoxide pour-on formulation (mineral oil solvent) (hereinafter referred to as 5P/5PB); or (3) Synergized Delice® (1% permethrin+1% piperonyl butoxide) (positive control). There were 31 animals in group 2 and 27 animals in group 3. Each animal in group 2 received 30 ml of the insecticide formulation; each animal in group (3) received 0.5 oz. (15 ml)/100 lb. body weight. Each animal was dosed individually based upon its estimated weight. The solutions of 5P/5PB and Synergized DeLice® were poured along the backline of each animal.

Total horn fly counts were obtained by counting flies on the entire body of ten randomly selected animals in each treatment group. The same ten animals were not used at each designated counting period. The following equation was used to evaluate efficacy for each week:

$$\text{Percent Efficacy} = \frac{\text{Mean flies from ten controls} - \text{Mean flies from ten treated}}{\text{Mean flies from ten controls}} \times 100$$

Counts for each test period were discontinued when efficacy was determined to be similar to that of the controls.

Pretreatment horn fly counts had shown that natural infestations of horn flies were relatively heavy and evenly distributed from one pasture to another. The data are presented in Table 1 below:

TABLE 1

| Animal Rep. No. | Week 0 Pretreatment Horn Fly Counts | | |
|---|---|---|---|
| | Con* | 5P/5PB* | S-DELICE* |
| 1 | 300 | 300 | 250 |
| 2 | 300 | 300 | 200 |
| 3 | 300 | 200 | 250 |
| 4 | 200 | 300 | 200 |
| 5 | 300 | 350 | 300 |
| 6 | 300 | 400 | 250 |
| 7 | 300 | 300 | 300 |
| 8 | 300 | 250 | 250 |
| 9 | 400 | 300 | 200 |
| 10 | 300 | 300 | 300 |
| Mean | 300 | 300 | 250 |

*CON = No insecticide treatment
5P/5PB = 5% permethrin + 5% piperonyl butoxide pour-on applied at a rate of 30 ml/head along the back line, (n = 31)
S-DELICE = Synergized Delice pour-on (1% permethrin + 1% piperonyl butoxide) applied at the rate of ½ oz(15 ml)/100 lb b.w., not to exceed 5 oz. (150 ml), (n = 27).

Post-treatment horn fly counts were obtained for nine weeks. Through week 6, 96–100% efficacy was achieved with treatment of 5P/5PB. Treatment with Synergized DeLice® was found to be 100% efficacious through the second week but then dropped off to 16% during the fourth week. The full results of the trial are presented in Table 2, below:

TABLE 2

| Animal Rep No. | Week 1 Horn Fly Counts | | |
|---|---|---|---|
| | CON* | 5P/5PB* t = 12 Apr | S-DELICE* t = 9 Apr |
| 1 | 300 | 0 | 0 |
| 2 | 280 | 0 | 0 |
| 3 | 350 | 0 | 0 |
| 4 | 200 | 0 | 0 |
| 5 | 400 | 0 | 0 |
| 6 | 330 | 0 | 0 |
| 7 | 350 | 0 | 0 |
| 8 | 390 | 0 | 0 |
| 9 | 350 | 0 | 0 |
| 10 | 300 | 0 | 0 |
| Mean | 325 | 0 | 0 |
| % Efficacy | | 100 | 100 |

| Animal Rep No. | Week 2 Horn Fly Counts | | |
|---|---|---|---|
| | CON* | 5P/5PB* | S-DELICE* |
| 1 | 350 | 0 | 0 |
| 2 | 300 | 0 | 0 |
| 3 | 350 | 0 | 0 |
| 4 | 350 | 0 | 0 |
| 5 | 350 | 0 | 0 |
| 6 | 400 | 0 | 0 |
| 7 | 500 | 0 | 0 |
| 8 | 350 | 0 | 0 |
| 9 | 200 | 0 | 0 |
| 10 | 350 | 0 | 0 |
| Mean | 350 | 0 | 0 |
| % Efficacy | | 100 | 100 |

| Animal Rep No. | Week 3 Horn Fly Counts | | |
|---|---|---|---|
| | CON* | 5P/5PB* | S-DELICE* |
| 1 | 600 | 0 | 20 |
| 2 | 450 | 0 | 24 |

TABLE 2-continued

| Rep No. | CON* | 5P/5PB* | S-DELICE* |
| --- | --- | --- | --- |
| 3 | 500 | 0 | 26 |
| 4 | 550 | 0 | 28 |
| 5 | 800 | 0 | 24 |
| 6 | 500 | 0 | 30 |
| 7 | 600 | 0 | 16 |
| 8 | 600 | 0 | 18 |
| 9 | 800 | 0 | 28 |
| 10 | 600 | 0 | 26 |
| Mean | 600 | 0 | 24 |
| % Efficacy |  | 100 | 96 |

| Animal | Week 4 Horn Fly Counts | | |
| --- | --- | --- | --- |
| Rep No. | CON* | 5P/5PB* | S-DELICE* |
| 1 | 600 | 0 | 500 |
| 2 | 650 | 0 | 500 |
| 3 | 700 | 0 | 400 |
| 4 | 550 | 0 | 300 |
| 5 | 600 | 0 | 500 |
| 6 | 450 | 0 | 600 |
| 7 | 600 | 0 | 500 |
| 8 | 650 | 0 | 700 |
| 9 | 500 | 0 | 500 |
| 10 | 650 | 0 | 500 |
| Mean | 595 | 0 | 500 |
| % Efficacy |  | 100 | 16 |

| Animal | Week 5 Horn Fly Counts | | |
| --- | --- | --- | --- |
| Rep No. | CON* | 5P/5PB* | S-DELICE* |
| 1 | 500 | 0 | 400 |
| 2 | 500 | 0 | 500 |
| 3 | 450 | 0 | 400 |
| 4 | 450 | 0 | 300 |
| 5 | 400 | 0 | 350 |
| 6 | 450 | 0 | 400 |
| 7 | 300 | 0 | 450 |
| 8 | 400 | 0 | 500 |
| 9 | 650 | 0 | 300 |
| 10 | 400 | 0 | 400 |
| Mean | 450 | 0 | 400 |
| % Efficacy |  | 100 | 11 |

| Animal | Week 6 Horn Fly Counts | | |
| --- | --- | --- | --- |
| Rep No. | CON* | 5P/5PB* | S-DELICE* |
| 1 | 600 | 20 | 600 |
| 2 | 600 | 16 | 600 |
| 3 | 650 | 22 | 550 |
| 4 | 700 | 18 | 500 |
| 5 | 500 | 24 | 650 |
| 6 | 500 | 16 | 700 |
| 7 | 650 | 28 | 600 |
| 8 | 700 | 20 | 600 |
| 9 | 600 | 20 | 750 |
| 10 | 500 | 16 | 450 |
| Mean | 600 | 20 | 600 |
| % Efficacy |  | 97 | 0 |

| Animal | Week 7 Horn Fly Counts | | |
| --- | --- | --- | --- |
| Rep No. | CON* | 5P/5PB* | S-DELICE* |
| 1 | 600 | 40 | 700 |
| 2 | 630 | 50 | 650 |
| 3 | 650 | 40 | 750 |
| 4 | 700 | 46 | 600 |
| 5 | 580 | 42 | 500 |
| 6 | 600 | 36 | 640 |
| 7 | 640 | 30 | 700 |
| 8 | 600 | 38 | 650 |
| 9 | 650 | 42 | 530 |
| 10 | 600 | 36 | 600 |
| Mean | 625 | 40 | 632 |
| % Efficacy |  | 94 | 0 |

| Animal | Week 8 Horn Fly Counts | | |
| --- | --- | --- | --- |
| Rep No. | CON* | 5P/5PB* | S-DELICE* |
| 1 | 500 | 120 | 500 |
| 2 | 600 | 100 | 550 |
| 3 | 500 | 106 | 500 |
| 4 | 450 | 110 | 450 |
| 5 | 500 | 116 | 600 |
| 6 | 550 | 100 | 600 |
| 7 | 650 | 90 | 500 |
| 8 | 400 | 124 | 400 |
| 9 | 450 | 100 | 400 |
| 10 | 400 | 134 | 500 |
| Mean | 500 | 110 | 500 |
| % Efficacy |  | 78 | 0 |

| Animal | Week 9 Horn Fly Counts | | |
| --- | --- | --- | --- |
| Rep No. | CON* | 5P/5PB* | S-DELICE* |
| 1 | 700 | 400 | 800 |
| 2 | 650 | 450 | 700 |
| 3 | 700 | 500 | 700 |
| 4 | 750 | 300 | 600 |
| 5 | 600 | 400 | 650 |
| 6 | 750 | 550 | 700 |
| 7 | 800 | 400 | 650 |
| 8 | 700 | 350 | 700 |
| 9 | 600 | 400 | 650 |
| 10 | 750 | 250 | 850 |
| Mean | 700 | 400 | 700 |
| % Efficacy |  | 43 | 0 |

*CON = No insecticide treatment
5P/5PB = 5% permethrin + 5% piperonyl butoxide pour-on applied at a rate of 30 ml/head along the back line, (n = 31)
S-DELICE = Synergized Delice pour-on (1% permethrin + 1% piperonyl butoxide) applied at the rate of ½ oz (5 ml)/100 lb b.w., not to exceed 5 oz. (150 ml) (n = 27).

EXAMPLE 2

Herds of cattle were segregated by pasture and treated with one of the following formulations: (1) 5% permethrin pour-on formulation (mineral oil solvent) (hereinafter referred to as 5P) or (2) Delice® (1% permethrin). There were 32 animals in group 1 and 24 animals in group 2. Each animal in group 2 received 30 ml of the insecticide formulation; each animal in group 1 received 0.5 oz. (15 ml)/100 lb. body weight. Each animal was dosed individually based upon its estimated weight. The solutions of 5P and DeLice® were poured along the backline of each animal.

Total horn fly counts were obtained by counting flies on the entire body of ten randomly selected animals in each treatment group. The same ten animals were not used at each designated counting period. The equation set forth in Example 1, above, was used to evaluate efficacy for each week.

Post-treatment horn fly counts were obtained for five weeks. Through this time, 94–100% efficacy was achieved with treatment of 5P. Treatment with DeLice® was found to be 100% efficacious through the second week but then dropped off to 57% during the fifth week. A summary of the results of the trial are presented in Table 3, below:

TABLE 3

| Treatment | Percent Reduction of Horn Flies on Cattle | | | | | |
|---|---|---|---|---|---|---|
| | Week 0 | Week 1 | Week 2 | Week 3 | Week 4 | Week 5 |
| 5% Permethrin | 0 | 100 | 100 | NO Count | 99 | 94 |
| 1% Permethrin | 0 | 100 | 100 | No Count | 68 | 57 |

EXAMPLE 3

Efficacy Evaluation of 5% Permethrin with 5% Piperonyl Butoxide Against Horn Flies A study was conducted to compare the efficacy of a 5% permethrin+5% piperonyl butoxide pour-on with two commercially available pour-on products, Synergized Delice® (1% permethrin/1% piperonyl butoxide) and Delice® (1% permethrin), against horn flies on cattle.

The cattle were divided into four herds. Brood cows in all four herds averaged 1,000 horn flies per head and the bulls averaged 10,000 flies per head. The herds were treated as follows:

(1) control herd: received no treatment. This herd consisted of 50 animals.

(2) Synergized DeLice® was applied along the backline according to label recommendations at 15 ml/1000 lbs body weight not to exceed 150 ml/head. This test herd consisted of 27 animals.

(3) 5% permethrin and 5% piperonyl butoxide formulation was applied as a pour-on along the backline at the rate of 3 ml/100 lbs of body weight not to exceed 30 ml/head. This test herd consisted of 26 animals.

(4) Delice® was applied along the backline according to label recommendations of 15 ml/100 pounds of body weight not to exceed 150 ml/head. This test herd consisted of 26 animals.

Horn fly infestations consisted of natural field populations. Infestation levels were determined prior to treatment and weekly thereafter by counting the total number of horn flies on the entire body of ten randomly selected animals in each treatment group. The percent horn fly control then was calculated in accordance with the formula presented in example 1, above.

As shown in the attached table, the pour-on formulation of 5% permethrin and 5% piperonyl butoxide applied at the rate of only 3 ml/100 pounds of body weight provided the most effective horn fly treatment, with 100% fly control for four weeks after treatment. After four weeks the Synergized Delice® provided 30% fly control and the Delice® provided 80% control. The results are summarized in Table 4 below:

TABLE 4

| Treatment | Percent Reduction of Horn Flies on Cattle | | | | | |
|---|---|---|---|---|---|---|
| | Week 0 | Week 1 | Week 2 | Week 3 | Week 4 | Week 5 |
| 5% Permethrin/5% pbo | 0 | 100 | 100 | 100 | 100 | 62 |
| 1% Permethrin | 0 | 100 | 100 | 90 | 80 | 62 |
| 1% Perm./1% pbo | 0 | 100 | 100 | 100 | 30 | 0 |

EXAMPLE 4

Efficacy of Concentrated Ectoparasiticide Formulation Against Cattle Lice

A study was conducted to compare the efficacy of a 5% permethrin+5% piperonyl butoxide pour-on with a commercial available pour-on product, Synergized DeLice®, against chewing lice and sucking lice on cattle.

The cattle were divided into three groups of eight animals each. The cattle were naturally infested with lice from the genera Bovicola (chewing lice), Haematopinus (sucking lice), and/or Linognathus (sucking lice). Counts were taken per genera. The cattle were treated as follows:

(1) control herd: received no treatment.

(2) Permethrin pour-on (5% permethrin+5% piperonyl butoxide) (5P/5PB) applied at a rate of three ml per 100 lb. body weight, not to exceed 30 ml/head.

(3) Permethrin pour-on (1% permethrin+1% piperonyl butoxide) (1P/1PB) (Synergized DeLice®) applied along the backline according to label recommendations at 15 ml/100 lbs body weight not to exceed 150 ml/head.

Infestation levels of both the chewing and sucking lice were determined prior to treatment and weekly thereafter by counting the total number of each type of lice on various preselected parts of the body of each animal in each treatment group. The percent lice control then was calculated in accordance with the formula presented in example 1, above.

As shown in the tables below, the pour-on formulation of the 5% permethrin and 5% piperonyl butoxide was not statistically more effective than the synergized DeLice® in controlling lice infestations. This example and Example 5, below, show that the present invention is specific to controlling fly infestations.

TABLE 5

Chewing lice counts from cattle receiving no treatment (control) or treated with different formulations of permethrin applied as a pour-on. Counts represent means from lice located on various parts of the body.

| Animal NO | TREATMENT NO | DOSE (ml) | PRE-TRT | DAY 0 | Day 14 | Day 28 | Day 44 | Day 56 |
|---|---|---|---|---|---|---|---|---|
| 334 | CONTROL | 0 | 0 | 0 | 8 | 7 | 0 | 7 |
| 365 | CONTROL | 0 | 6 | 0 | 10 | 18 | 10 | 13 |
| 318 | CONTROL | 0 | 0 | 0 | 16 | 13 | 7 | 11 |
| 360 | CONTROL | 0 | 8 | 0 | 10 | 15 | 0 | 11 |
| 312 | CONTROL | 0 | 3 | 0 | 8 | 12 | 3 | 2 |
| 293 | CONTROL | 0 | 10 | 0 | 23 | 12 | 4 | 10 |

TABLE 5-continued

Chewing lice counts from cattle receiving no treatment (control) or treated with different formulations of permethrin applied as a pour-on. Counts represent means from lice located on various parts of the body.

| Animal NO | TREATMENT NO | DOSE (ml) | PRE-TRT | DAY 0 | Day 14 | Day 28 | Day 44 | Day 56 |
|---|---|---|---|---|---|---|---|---|
| 326 | CONTROL | 0 | 4 | 0 | 16 | 13 | 7 | 0 |
| 308 | CONTROL | 0 | 7 | 0 | 16 | 12 | 9 | 10 |
|  | MEAN | 0 | 4.75 | 5 | 13.38 | 12.75 | 5 | 8 |
| 309 | 5% P/5% PBO | 16.88 | 26 | 9 | 9 | 0 | 0 | 0 |
| 383 | 5% P/5% PBO | 14.82 | 0 | 8 | 8 | 0 | 0 | 0 |
| 322 | 5% P/5% PBO | 10.65 | 0 | 13 | 0 | 0 | 0 | 0 |
| 321 | 5% P/5% PBO | 12.36 | 0 | 7 | 4 | 0 | 0 | 0 |
| 320 | 5% P/5% PBO | 12.84 | 12 | 6 | 7 | 0 | 0 | 0 |
| 352 | 5% P/5% PBO | 12.06 | 10 | 15 | 7 | 0 | 0 | 0 |
| 381 | 5% P/5% PBO | 12.24 | 5 | 7 | 5 | 0 | 0 | 0 |
| 361 | 5% P/5% PBO | 10.98 | 8 | 7 | 4 | 0 | 0 | 0 |
|  | MEAN | 12.85 | 7.63 | 9 | 5.5 | 0 | 0 | 0 |
| PERCENT CONTROL |  |  | 0% | 0% | 59% | 100% | 100% | 100% |
| 362 | 1% P/1% PBO | 76.9 | 0 | 4 | 0 | 0 | 0 | 0 |
| 384 | 1% P/1% PBO | 81.7 | 10 | 8 | 0 | 0 | 0 | 0 |
| 353 | 1% P/1% PBO | 63.4 | 6 | 0 | 4 | 0 | 1 | 0 |
| 305 | 1% P/1% PBO | 58.5 | 3 | 3 | 0 | 0 | 0 | 0 |
| 382 | 1% P/1% PBO | 63.4 | 0 | 7 | 4 | 0 | 0 | 0 |
| 311 | 1% P/1% PBO | 57.3 | 8 | 5 | 0 | 0 | 1 | 0 |
| 313 | 1% P/1% PBO | 56.2 | 10 | 8 | 0 | 0 | 0 | 0 |
| 317 | 1% P/1% PBO | 62.2 | 0 | 5 | 3 | 0 | 0 | 0 |
|  | MEAN | 64.95 | 4.63 | 5 | 1.38 | 0 | 0.25 | 0 |
| PERCENT CONTROL |  |  | 3% | 0% | 90% | 100% | 95% | 100% |

TABLE 6

Sucking lice counts from cattle receiving no treatment (control or treated with different formulations of permethrin applied as a pour-on. Counts represent means from lice located on various parts of the body.

| Animal NO | TREATMENT NO | DOSE (ml) | PRE-TRT | DAY 0 | Day 14 | Day 28 | Day 44 | Day 56 |
|---|---|---|---|---|---|---|---|---|
| 293 | CONTROL | 0 | 123 | 118 | 115 | 116 | 105 | 124 |
| 308 | CONTROL | 0 | 54 | 65 | 71 | 90 | 61 | 109 |
| 312 | CONTROL | 0 | 17 | 21 | 11 | 19 | 4 | 2 |
| 318 | CONTROL | 0 | 68 | 75 | 98 | 55 | 24 | 20 |
| 326 | CONTROL | 0 | 89 | 78 | 50 | 56 | 27 | 37 |
| 334 | CONTROL | 0 | 9 | 23 | 25 | 12 | 4 | 8 |
| 360 | CONTROL | 0 | 109 | 118 | 125 | 113 | 50 | 29 |
| 365 | CONTROL | 0 | 148 | 146 | 143 | 118 | 86 | 54 |
|  | MEAN | 0 | 77.13 | 79.88 | 79.75 | 72.38 | 45.13 | 47.88 |
| 309 | 5% P/5% PBO | 16.88 | 77 | 101 | 43 | 9 | 17 | 18 |
| 320 | 5% P/5% PBO | 14.82 | 69 | 76 | 30 | 3 | 8 | 12 |
| 321 | 5% P/5% PBO | 10.65 | 84 | 102 | 58 | 2 | 11 | 21 |
| 322 | 5% P/5% PBO | 12.36 | 102 | 78 | 43 | 0 | 0 | 6 |
| 352 | 5% P/5% PBO | 12.84 | 82 | 72 | 38 | 4 | 0 | 6 |
| 361 | 5% P/5% PBO | 12.06 | 127 | 114 | 53 | 4 | 13 | 8 |
| 381 | 5% P/5% PBO | 12.24 | 98 | 108 | 51 | 19 | 7 | 9 |
| 383 | 5% P/5% PBO | 10.98 | 21 | 70 | 35 | 0 | 0 | 7 |
|  | MEAN | 12.85 | 82.5 | 90.13 | 43.88 | 5.13 | 7 | 10.88 |
| PERCENT CONTROL |  |  | 0 | 0 | 45% | 93% | 84% | 77% |
| 305 | 1% P/1% PBO | 76.9 | 53 | 65 | 0 | 4 | 0 | 0 |
| 311 | 1% P/1% PBO | 81.7 | 119 | 95 | 28 | 6 | 2 | 10 |
| 313 | 1% P/1% PBO | 63.4 | 130 | 102 | 25 | 8 | 10 | 9 |
| 317 | 1% P/1% PBO | 58.5 | 59 | 76 | 8 | 5 | 0 | 0 |
| 353 | 1% P/1% PBO | 63.4 | 96 | 92 | 42 | 9 | 4 | 2 |
| 362 | 1% P/1% PBO | 57.3 | 81 | 66 | 12 | 0 | 0 | 0 |
| 382 | 1% P/1% PBO | 56.2 | 29 | 61 | 11 | 0 | 0 | 1 |
| 384 | 1% P/1% PBO | 62.2 | 115 | 118 | 48 | 3 | 4 | 8 |
|  | MEAN | 64.95 | 85.24 | 84.38 | 21.75 | 4.38 | 2.5 | 3.75 |
| PERCENT CONTROL |  |  | 0 | 0 | 73% | 94% | 94% | 92% |

EXAMPLE 5

Efficacy Evaluation of Ectoparasiticides in the Control of *Amblyomma americanum* on Cattle Cattle naturally infested with the three host tick, *Amblyomma americanum*, were randomly assigned to one of the following treatment groups: 1) control, no treatment; 2) Synergized Delice® (1% permethrin+1% piperonyl butoxide) applied at a rate of 15 ml/100 lb. body weight, maximum 150 ml; or 3) 5% permethrin+5% piperonyl butoxide (5P/5PB) applied at a rate of 3 ml/100 lb. body weight; maximum 30 ml. All treatments given were single treatments applied along the backline from the poll to the base of the tail (i.e., pour-on). There were eleven cattle in each group.

At 14 days post-treatment, the efficacy of the Delice® and 5P/5PB against nymphs was 77% and 76%. Day 14 efficacy against adult ticks was 58% and 61%, respectively. At day 21 tick populations on the controls declined to the point where valid observations were unattainable.

I claim:

1. In a method for controlling infestations of flies on an animal by applying a dose of a composition comprising about 0.5% to about 1.5% of an ectoparasiticide and a carrier onto the skin or coat of an animal, the improvement which comprises:

increasing the concentration of the about 0.5% to about 1.5% ectoparasiticide to about 3% to about 90% by weight of the composition and proportionately reducing the volume of the composition administered to the animal such that the animal receives the same amount of the ectoparasiticide as it would have received prior to the concentration of the ectoparasiticide.

2. A method in accordance with claim 1, wherein the ectoparasiticide is concentrated to produce a composition comprising about 5% to about 50% ectoparasiticide.

3. A method in accordance with claim 2, wherein the ectoparasiticide is concentrated to produce a composition comprising about 5% to about 30% ectoparasiticide.

4. A method in accordance with claim 1, wherein the ectoparasiticide comprises an organophosphate or a pyrethroid.

5. A method in accordance with claim 4, wherein the organophosphate comprises a phosphate, phosphothioate or phosphothionate compound.

6. A method in accordance with claim 5, wherein the organophosphate comprises chloryriphos, pirimiphos-methyl, diazinon, or tetrachlorvinphos.

7. A method in accordance with claim 4, wherein the pyrethroid comprises an active insecticidal constituent of pyrethrum flowers or a synthetic version of such a compound.

8. A method in accordance with claim 7, wherein the pyrethroid comprises permethrin.

9. A method in accordance with claim 7, wherein the composition further comprises a pesticide synergist.

10. A method in accordance with claim 9, wherein the pesticide synergist comprises piperonyl butoxide.

11. A method in accordance with claim 1, wherein the composition is in the form of a solution.

12. A method in accordance with claim 1, wherein the composition is in the form of a powder.

13. In a method for controlling infestations of flies on an animal by applying a dose of a solution comprising about 0.5% to about 1.5% permethrin and piperonyl butoxide onto the skin or coat of the animal, the improvement which comprises increasing the concentration of the about 0.5% to about 1.5% permethrin to about 3% to about 30% of the solution, increasing the concentration of the piperonyl butoxide to equal that of the permethrin and proportionately reducing the volume of the solution administered to the animal such that the animal receives the same amount of the permethrin as it would have received prior to the concentration of the permethrin.

* * * * *

UNITED STATES PATENT AND TRADEMARK OFFICE
CERTIFICATE OF CORRECTION

PATENT NO. : 5,750,514
DATED : May 12, 1998
INVENTOR(S) : Jeffery A. Meyer

It is certified that error appears in the above-identified patent and that said Letters Patent is hereby corrected as shown below:

Column 4, line 31, insert "Table 2: Horn fly counts post-treatment. Ten animals from each herd were selected randomly for fly counts at each counting period."
Column 4, Table 2, first column, delete "G" and insert therefor --6--.
Column 9, Table 6, in the second line, "(control" should read --(control)--.

Signed and Sealed this

Twenty-fourth Day of November, 1998

Attest:

BRUCE LEHMAN

*Attesting Officer*    *Commissioner of Patents and Trademarks*